(12) United States Patent
Choi et al.

(10) Patent No.: US 11,337,609 B2
(45) Date of Patent: May 24, 2022

(54) TEXTURE INTERFACE FOR MEASURING BIO-SIGNAL AND BIO-SIGNAL MEASURING APPARATUS INCLUDING THE SAME

(71) Applicant: SAMSUNG ELECTRONICS CO., LTD., Suwon-si (KR)

(72) Inventors: Chang Mok Choi, Suwon-si (KR); Jeong Eun Hwang, Suwon-si (KR); Byung Hoon Ko, Hwaseong-si (KR); Jong Wook Lee, Suwon-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 339 days.

(21) Appl. No.: 16/586,159

(22) Filed: Sep. 27, 2019

(65) Prior Publication Data

US 2020/0237222 A1    Jul. 30, 2020

(30) Foreign Application Priority Data

Jan. 25, 2019    (KR) .................... 10-2019-0009844

(51) Int. Cl.
*A61B 5/00*      (2006.01)
*A61B 5/024*     (2006.01)
*G06F 3/01*      (2006.01)

(52) U.S. Cl.
CPC .......... *A61B 5/0015* (2013.01); *A61B 5/0064* (2013.01); *A61B 5/02416* (2013.01);
(Continued)

(58) Field of Classification Search
None
See application file for complete search history.

(56) References Cited

U.S. PATENT DOCUMENTS 4,938,218 A * 7/1990 Goodman .......... A61B 5/14542
                                                    600/338
5,099,842 A * 3/1992 Mannheimer ........ A61B 5/6834
                                                    600/323
(Continued)

FOREIGN PATENT DOCUMENTS

JP    2004-021563 A    1/2004
JP    2010-257163 A    11/2010
(Continued)

OTHER PUBLICATIONS

Communication dated Jun. 9, 2020 issued by the European Intellectual Property Office in counterpart European Application No. 20153129.0.

(Continued)

*Primary Examiner* — Carl H Layno
*Assistant Examiner* — Manolis Pahakis
(74) *Attorney, Agent, or Firm* — Sughrue Mion, PLLC

(57) ABSTRACT

A bio-signal measuring apparatus may include: a finger contact surface configured to be in contact with a finger of a user; an optical sensor configured to be disposed underneath the finger contact surface and sense a light when the light is reflected from the user, and a textured area formed on the finger contact surface at a boundary of the optical sensor, and configured to provide a texture different from a texture of a remaining area of the finger contact surface other than the textured area, so as to allow the user to feel a tactile sensation from the textured area when the finger is in contact with the finger contact surface.

12 Claims, 22 Drawing Sheets

(52) U.S. Cl.
CPC ........ *A61B 5/02427* (2013.01); *A61B 5/0006* (2013.01); *A61B 5/6826* (2013.01); *A61B 5/6898* (2013.01); *G06F 3/016* (2013.01)

(56) References Cited

U.S. PATENT DOCUMENTS

| | | | | |
|---|---|---|---|---|
| 5,187,748 | A * | 2/1993 | Lee | G06K 9/00046 382/127 |
| 5,402,777 | A * | 4/1995 | Warring | A61B 5/02433 424/449 |
| 5,448,649 | A * | 9/1995 | Chen | G06K 9/00046 356/71 |
| 5,584,296 | A * | 12/1996 | Cui | A61B 5/14552 356/41 |
| 5,734,625 | A * | 3/1998 | Kondo | A61B 5/02438 368/10 |
| 5,766,131 | A * | 6/1998 | Kondo | A61B 5/02416 600/310 |
| 5,823,952 | A * | 10/1998 | Levinson | A61B 5/14552 600/338 |
| 6,011,860 | A * | 1/2000 | Fujieda | G06K 9/00899 382/126 |
| 6,223,063 | B1 * | 4/2001 | Chaiken | A61B 5/02427 600/310 |
| 6,324,310 | B1 * | 11/2001 | Brownlee | G06K 9/00026 382/312 |
| 6,522,773 | B1 * | 2/2003 | Houdeau | G06K 9/0002 382/124 |
| 6,525,386 | B1 * | 2/2003 | Mills | B29C 45/401 257/100 |
| 6,847,350 | B2 * | 1/2005 | Van Brocklin | G06F 1/1616 345/156 |
| 7,227,978 | B2 * | 6/2007 | Komatsuzaki | G06K 9/00026 382/124 |
| RE44,856 | E * | 4/2014 | Adelson | G06K 9/00006 348/135 |
| 9,122,308 | B2 * | 9/2015 | Lee | G06F 3/016 |
| 9,459,221 | B2 | 10/2016 | Matsumoto et al. | |
| 10,506,961 | B1 * | 12/2019 | Schoess | A61B 5/0051 |
| 10,599,911 | B2 * | 3/2020 | Ryshtun | G06K 9/00087 |
| 10,827,979 | B2 * | 11/2020 | LeBoeuf | A61B 5/6817 |
| 2003/0015646 | A1 * | 1/2003 | Deconde | G06K 9/0002 250/208.1 |
| 2003/0076303 | A1 * | 4/2003 | Huppi | G06F 3/0362 345/163 |
| 2003/0118219 | A1 * | 6/2003 | Higuchi | G06K 9/00046 382/125 |
| 2004/0057604 | A1 | 3/2004 | David et al. | |
| 2004/0170307 | A1 * | 9/2004 | Manansala | G06K 9/00026 382/126 |
| 2004/0208348 | A1 * | 10/2004 | Baharav | G06K 9/00026 382/124 |
| 2005/0139685 | A1 * | 6/2005 | Kozlay | G06K 19/077 235/492 |
| 2005/0180609 | A1 * | 8/2005 | Bolis | H01L 23/3121 382/116 |
| 2005/0271258 | A1 * | 12/2005 | Rowe | G06K 9/2018 382/124 |
| 2006/0211922 | A1 * | 9/2006 | Al-Ali | A61B 5/14551 600/310 |
| 2007/0073117 | A1 * | 3/2007 | Raridan | A61B 5/14552 600/310 |
| 2007/0078311 | A1 * | 4/2007 | Al-Ali | A61B 5/14532 600/310 |
| 2007/0142717 | A1 * | 6/2007 | Lowery | A61B 5/6833 600/323 |
| 2007/0147666 | A1 * | 6/2007 | Chiu | G06K 9/00053 382/124 |
| 2007/0260129 | A1 * | 11/2007 | Chin | A61B 5/4362 600/323 |
| 2008/0025582 | A1 * | 1/2008 | Kobayashi | G06K 9/00013 382/124 |
| 2008/0148059 | A1 * | 6/2008 | Shapiro | G06F 21/32 713/186 |
| 2008/0226132 | A1 | 9/2008 | Gardner | |
| 2009/0067690 | A1 * | 3/2009 | Mainguet | G06K 9/00053 382/124 |
| 2009/0074263 | A1 * | 3/2009 | Higuchi | G06K 9/00026 382/126 |
| 2009/0153297 | A1 * | 6/2009 | Gardner | G06K 19/07732 340/5.83 |
| 2009/0166784 | A1 * | 7/2009 | Honda | H01L 31/0203 257/432 |
| 2009/0240125 | A1 | 9/2009 | Such et al. | |
| 2010/0004518 | A1 * | 1/2010 | Vo | A61B 5/70 600/310 |
| 2010/0245237 | A1 | 9/2010 | Nakamura | |
| 2011/0215484 | A1 * | 9/2011 | Bond | H01L 27/20 257/787 |
| 2011/0254758 | A1 * | 10/2011 | Lin | G02B 26/001 345/84 |
| 2011/0298711 | A1 * | 12/2011 | Dean | G06F 3/0304 345/161 |
| 2012/0296178 | A1 | 11/2012 | Lamego et al. | |
| 2013/0234825 | A1 * | 9/2013 | Malhotra | G06K 9/00006 340/5.53 |
| 2013/0267854 | A1 * | 10/2013 | Johnson | A61B 5/0064 600/473 |
| 2013/0307818 | A1 * | 11/2013 | Pope | G06K 9/00053 345/174 |
| 2014/0135602 | A1 * | 5/2014 | Lemke | A61B 5/0205 600/324 |
| 2014/0275872 | A1 * | 9/2014 | Merritt | A61B 5/1455 600/322 |
| 2014/0292396 | A1 * | 10/2014 | Bruwer | H03K 17/962 327/517 |
| 2014/0333332 | A1 | 11/2014 | Matsumoto et al. | |
| 2015/0104083 | A1 * | 4/2015 | Gu | G06K 9/0004 382/124 |
| 2015/0220109 | A1 * | 8/2015 | von Badinski | A61B 5/021 340/539.12 |
| 2015/0293592 | A1 * | 10/2015 | Cheong | G06F 3/0416 345/173 |
| 2015/0340351 | A1 * | 11/2015 | Rossi | H01L 25/167 257/82 |
| 2016/0034742 | A1 * | 2/2016 | Kim | H04B 1/385 382/124 |
| 2016/0103505 | A1 * | 4/2016 | Fukumoto | G06F 3/03547 345/161 |
| 2016/0140379 | A1 * | 5/2016 | Pedersen | G06F 21/316 726/19 |
| 2016/0166161 | A1 | 6/2016 | Yang et al. | |
| 2016/0198996 | A1 * | 7/2016 | Dullen | A61B 5/4824 600/301 |
| 2016/0317060 | A1 * | 11/2016 | Connor | A61B 5/681 |
| 2016/0335470 | A1 * | 11/2016 | Park | H01L 24/16 |
| 2017/0000350 | A1 * | 1/2017 | Kwon | A61B 5/0261 |
| 2017/0076134 | A1 * | 3/2017 | Lin | H01L 24/73 |
| 2017/0135633 | A1 * | 5/2017 | Connor | G09B 19/0092 |
| 2017/0202464 | A1 * | 7/2017 | Tsao | A61B 5/282 |
| 2017/0308234 | A1 * | 10/2017 | Li | G06F 1/1626 |
| 2017/0325744 | A1 * | 11/2017 | Allec | A61B 5/6898 |
| 2017/0372123 | A1 * | 12/2017 | Kim | G06F 3/044 |
| 2018/0020979 | A1 * | 1/2018 | Wagner | A61B 5/0261 600/379 |
| 2018/0028122 | A1 | 2/2018 | Golda et al. | |
| 2018/0039127 | A1 * | 2/2018 | Eom | G06F 3/0443 |
| 2018/0064395 | A1 * | 3/2018 | Shim | A61B 5/0004 |
| 2018/0177413 | A1 * | 6/2018 | Kwon | A61B 5/022 |
| 2018/0235489 | A1 * | 8/2018 | Mouradian | A61B 5/02416 |
| 2019/0019072 | A1 * | 1/2019 | Bertiaux | G06K 19/0718 |
| 2019/0076032 | A1 | 3/2019 | Park et al. | |
| 2019/0150765 | A1 | 5/2019 | Fortin et al. | |
| 2019/0209029 | A1 | 7/2019 | Shimuta | |
| 2019/0274555 | A1 * | 9/2019 | Park | A61B 5/02255 |
| 2019/0392436 | A1 * | 12/2019 | Lee | G06K 19/07707 |
| 2020/0015690 | A1 | 1/2020 | Choi et al. | |
| 2020/0175242 | A1 * | 6/2020 | Uehara | G06F 3/0446 |

(56) References Cited

U.S. PATENT DOCUMENTS

2020/0196881 A1\* 6/2020 Zemel .................... A61B 5/145
2020/0383641 A1\* 12/2020 Hwang .................. A61B 5/681
2021/0059586 A1\* 3/2021 Marriott ............... A61B 5/6833

FOREIGN PATENT DOCUMENTS

| JP | WO2014/038212 A1 | 3/2014 |
|---|---|---|
| JP | 2017-139023 A | 8/2017 |
| KR | 10-2014-0094912 A | 7/2014 |
| KR | 10-1744311 B1 | 6/2017 |
| KR | 10-1762558 B1 | 7/2017 |
| KR | 10-2018-0076050 A | 7/2018 |
| KR | 10-2020-0007503 A | 1/2020 |
| KR | 10-2020-0054723 A | 5/2020 |
| KR | 10-2020-0091625 A | 7/2020 |
| WO | 2010/130115 A1 | 11/2010 |
| WO | 2014/129622 A1 | 8/2014 |
| WO | 2017/143366 A1 | 8/2017 |
| WO | 2018/066342 A1 | 4/2018 |

OTHER PUBLICATIONS

Communication dated Feb. 2, 2022 issued by the European Patent Office in counterpart European Application No. 20 153 129.0.

\* cited by examiner

TEXTURE INTERFACE FOR MEASURING BIO-SIGNAL AND BIO-SIGNAL MEASURING APPARATUS INCLUDING THE SAME

CROSS-REFERENCE TO RELATED APPLICATION(S)

This application claims priority from Korean Patent Application No. 10-2019-0009844, filed on Jan. 25, 2019, in the Korean Intellectual Property Office, the disclosure of which is incorporated herein by reference in its entirety.

BACKGROUND

1. Field

Apparatuses and methods consistent with example embodiments relate to technology for non-invasively measuring bio-signals from users.

2. Description of the Related Art

Recently, with an aging population, soaring medical costs, and a lack of medical personnel for specialized medical services, research is being actively conducted on IT-medical convergence technologies, in which IT technology and medical technology are combined. Particularly, monitoring of the health condition of the human body is not limited to medical institutions such as hospitals, but is expanding to mobile healthcare fields that may monitor a user's health condition anywhere and anytime in daily life at home or office.

Typical examples of bio-signals, which indicate the health condition of individuals, include an electrocardiography (ECG) signal, a photoplethysmogram (PPG) signal, an electromyography (EMG) signal, and the like, and various bio-signal measuring apparatuses have been developed to measure these signals in daily life. For example, as the bio-signal measuring apparatus measures a bio-signal from a user while the user's finger is in contact with an interface, health indicators may be estimated by non-invasively measuring the bio-signal.

In order to succeed in commercialization of the mobile healthcare technology, it is highly important to acquire stable and consistent bio-signals of the same health indicator when bio-signals are measured at different times. However, if excessive deviation occurs in contact position every time a user places a finger on an interface of a bio-signal measuring apparatus at different times, reproducibility of bio-signals is reduced, thus resulting in inaccurate estimation of health indicators. In order to ensure accurate estimation of health indicators, there is a need for a method of inducing a user's finger to come into contact with the same position on the interface every time the user measures bio-signals.

SUMMARY

According to an aspect of an example embodiment, there is provided a bio-signal measuring apparatus including: a finger contact surface configured to be in contact with a finger of a user; an optical sensor configured to be disposed underneath the finger contact surface and sense a light when the light is reflected from the user; and a texture area formed on the finger contact surface at a boundary of the optical sensor, and configured to provide a texture different from a texture of a remaining area of the finger contact surface other than the texture area, so as to allow the user to feel a tactile sensation from the texture area when the finger is in contact with the finger contact surface.

The texture area may be disposed to allow the user to feel the tactile sensation on both side portions of the finger when the finger is placed in a predetermined direction on the finger contact surface.

The finger contact surface may have a convex curvature that is curved in a direction parallel with a longitudinal direction of the finger when the finger is placed in a predetermined direction on the finger contact surface.

The texture area may be disposed at an apex portion of the finger contact surface.

The texture area may be protruded from the contact surface to provide the texture different from the texture of the remaining area.

The texture area may be depressed down into a lower position than the finger contact surface.

The texture area may have either a convex shape or a concave shape.

The texture area may be on an even level as the remaining area of the finger contact surface or may have a same curvature as the remaining area of the finger contact surface.

The texture area may have a different roughness from the remaining area of the finger contact surface.

The finger contact surface may include: a first light-transmitting area formed on a first portion of the finger contact surface; at least one second light-transmitting area which is spaced apart from the first light-transmitting area and is formed on a second portion of the finger contact surface; and a non-light-transmitting area formed on a third portion of the finger contact surface other than the first light-transmitting area and the second light-transmitting area.

The texture area may be disposed in the non-light-transmitting area.

The texture area may include a plurality of protrusions disposed to surround the first light-transmitting area.

The texture area may include a plurality of recesses disposed to surround the first light-transmitting area.

The bio-signal measuring apparatus may further include: a main body housing having an internal space and one open side; and a main body cover which has the finger contact surface on a first side, and covers the open side of the main body housing on a second side.

The main body cover may include: a cover member having holes, a size of which corresponds to each of the first light-transmitting area and the second light-transmitting area; and a light-transmitting member disposed inside each of the holes of the cover member.

The main body cover may include: a cover member having holes, a size of which corresponds to each of the first light-transmitting area and the second light-transmitting area; and a light-transmitting member which entirely covers the cover member.

The optical sensor may be a pulse wave sensor configured to measure a pulse wave signal from the user when the finger is in contact with the finger contact surface, and the bio-signal measuring apparatus further comprises a processor configured to obtain bio-information based on the pulse wave signal measured by the pulse wave sensor.

The finger contact surface may further include: a first light-transmitting area formed on a first portion of the finger contact surface; at least one second light-transmitting area which is spaced apart from the first light-transmitting area and is formed on a second portion of the finger contact surface; and a non-light-transmitting area formed on a third portion of the finger contact surface other than the first light-transmitting area and the second light-transmitting area.

The pulse wave sensor may include: a light source configured to emit the light onto tissue of the finger when the finger is in contact with the finger contact surface through the second light-transmitting area; and a detector configured to detect the light reflected from the tissue of the finger when the finger is in contact with the finger contact surface through the first light-transmitting area.

The pulse wave signal may be a photoplethysmography (PPG) signal.

Upon receiving a request for measuring a bio-signal, the processor may output action guide information for guiding the finger to come into contact with the finger contact surface.

BRIEF DESCRIPTION OF THE DRAWINGS

The above and/or other aspects will be more apparent by describing certain example embodiments, with reference to the accompanying drawings, in which.

Figure 1:
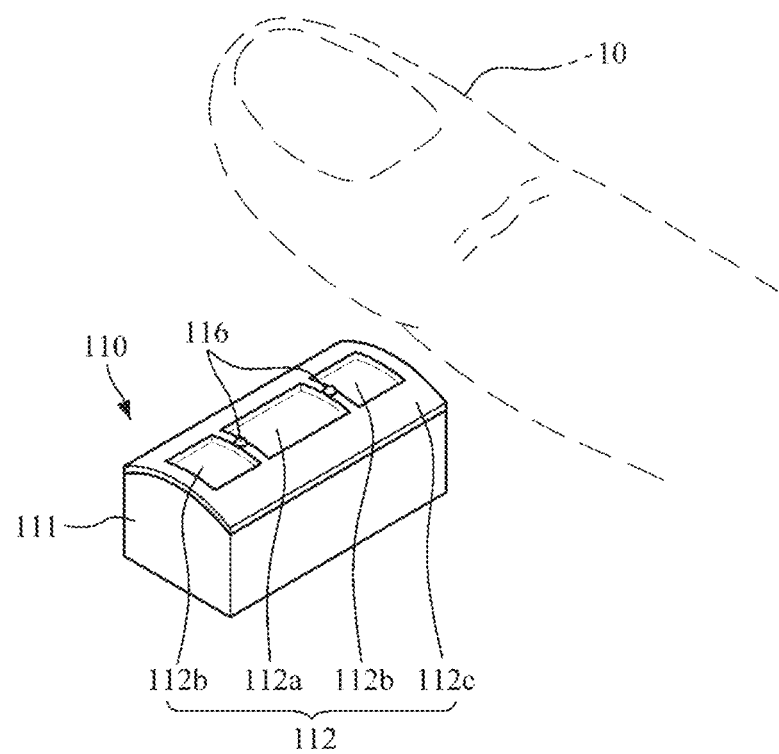
FIG. 1 is a perspective view of a texture interface for measuring a bio-signal according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations, such as "comprise" or "comprising", will be understood to imply the inclusion of stated elements but not the exclusion of any other elements. Terms, such as 'part' and 'module' denote units that process at least one function or operation and they may be implemented by using hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of a texture interface for measuring a bio-signal and a bio-signal measuring apparatus will be described in detail with reference to the accompanying drawings. The bio-signal measuring apparatus may be embedded in a terminal such as a smartphone, a tablet PC, a desktop computer, a laptop computer, and the like, or may be manufactured as an independent hardware device.

In the case where the bio-signal measuring apparatus is manufactured as an independent hardware device, the biosignal measuring apparatus may be implemented as a wearable device which may be worn on a user so that the user may easily measure bio-information while carrying the device. Examples of the wearable device may include a wristwatch-type wearable device, a bracelet-type wearable device a wristband-type wearable device, a ring-type wearable device, a glasses-type wearable device, a headband-type wearable device. and the like. However, the wearable device is not limited thereto, and may also be modified for various purposes such as a fixed-type device manufactured for use in medical institutions to measure and analyze bio-information.

Figure 2:
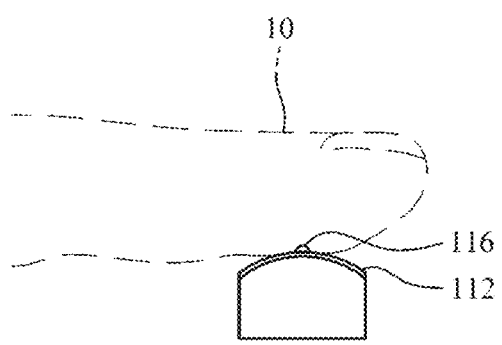
FIG. 2 is a side view of the texture interface of FIG. 1, showing a finger being in contact with a finger contact surface.
Figure 3:
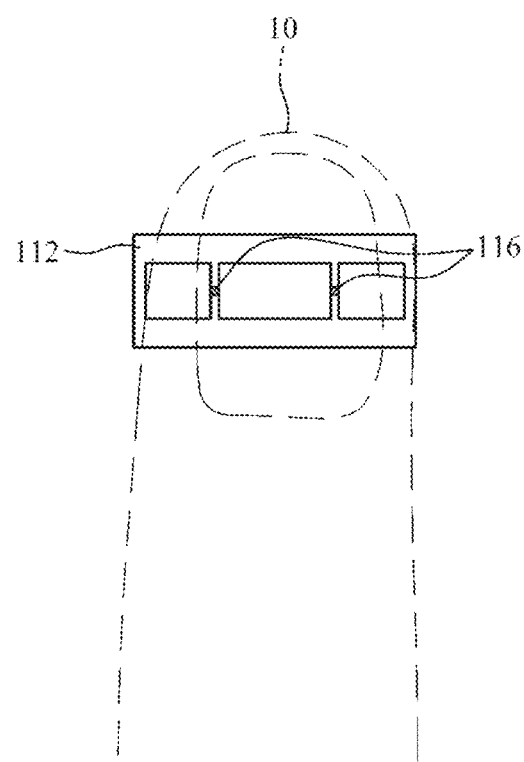
FIG. 3 is a plan view of the texture interface illustrated in FIG. 2.
Figure 4:
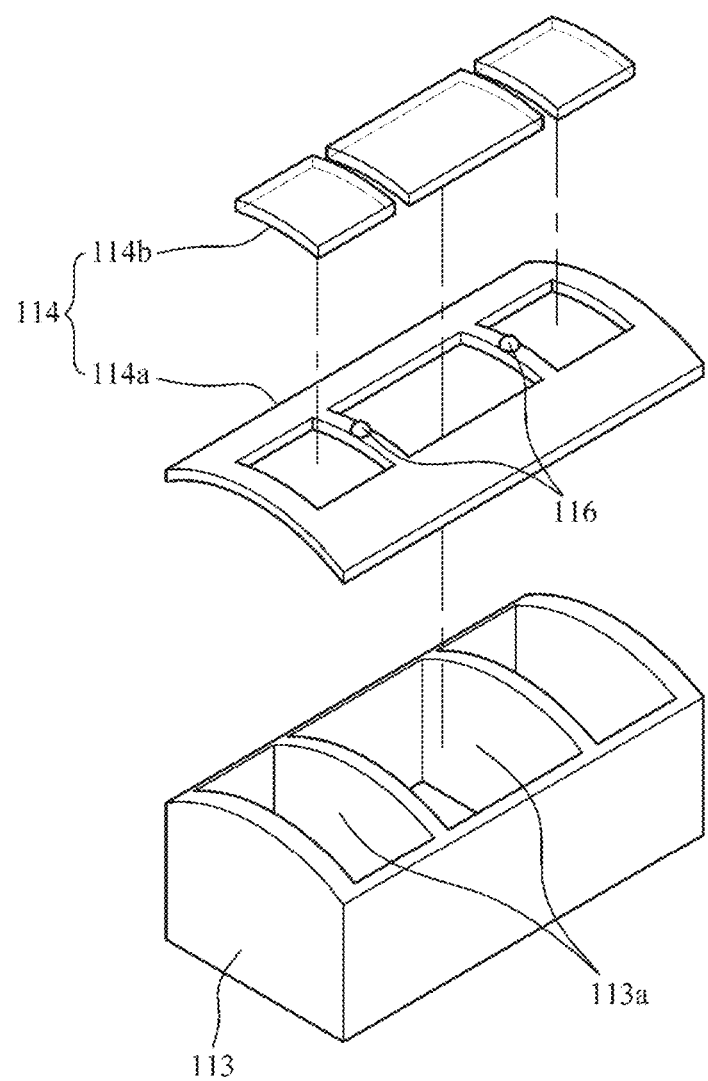
FIG. 4 is an exploded perspective view of the texture interface illustrated in FIG. 1.
Figure 5:
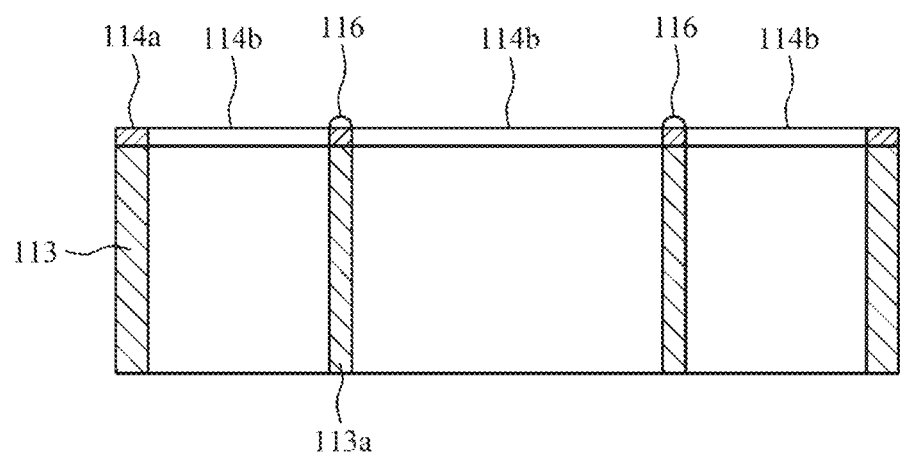
FIG. 5 is a cross-sectional view of the texture interface illustrated in FIG. 1.

FIG. 1 is a perspective view of a texture interface for measuring a bio-signal according to an example embodiment of the present disclosure; FIG. 2 is a side view of the texture interface of FIG. 1, showing a finger being in contact with a finger contact surface; FIG. 3 is a plan view of the texture interface of FIG. 1; FIG. 4 is an exploded perspective view of the texture interface illustrated in FIG. 1; and FIG. 5 is a cross-sectional view of the texture interface illustrated in FIG. 1.

Referring to FIGS. 1 to 5, the texture interface 110 for measuring a bio-signal according to an example embodiment of the present disclosure includes an interface main body 111 and a texture unit 116.

The interface main body 111 has a finger contact surface 112, on which a user's finger 10 is placed to come into contact with the finger contact surface 112. A finger is a mere example of a body part to be in contact with the interface main body 111. A different part of the body may be brought into contact with the interface main body 111. The texture unit 116 is formed at the finger contact surface 112 to allow a user to feel a tactile sensation on the finger 10 when the finger 10 is in contact with the finger contact surface 112.

The texture interface 110 for measuring a bio-signal may induce a user to place the finger 10 in the same position every time the user measures a bio-signal at different times, thereby improving reproducibility of the bio-signal. Here, when the finger 10 is placed in the set position on the finger contact surface 112, it is considered that the finger 10 contacts the finger contact surface 112 within an allowable range of the set position.

For example, when a user places the center of the distal phalanx of the finger 10 in the set position on the finger contact surface 112 to measure a bio-signal, the texture unit 116 provides tactile stimulation to a corresponding portion of the finger 10. Accordingly, when a user tries to measure a bio-signal for the first time, the user may recognize and remember a portion, to which tactile stimulation is provided by the texture unit 116.

In a subsequent attempt to measure a bio-signal, when the user places the finger 10 in the remembered position on the finger contact surface 112, to which tactile stimulation is provided by the texture unit 116, the center of the distal phalanx of the finger 10 may be aligned with the set position on the finger contact surface 112.

In this manner, every time the user measures a bio-signal at different times, the texture unit 116 may enable the user to place the center of the distal phalanx of the finger 10 consistently in the same position on the finger contact surface 112. Further, when the bio-signals are measured at different times, stable and consistent bio-signals may be acquired under the same health condition of the user, thereby allowing accurate estimation of health indicators.

The finger contact surface 112 may be formed with a smooth surface except for a portion where the texture unit 116 is formed. When the finger 10 is placed in a predetermined direction for contact with the finger contact surface 112, the finger contact surface 112 may have a convex curvature in a direction parallel with a longitudinal direction of the finger 10.

For convenience of explanation, with respect to a predetermined direction, in which the finger 10 is placed on the finger contact surface 112, a direction parallel with the longitudinal direction of the finger 10 is defined as a first direction, and a direction parallel with the width direction of the finger 10 is defined as a second direction. In this case, the finger contact surface 112 may have a convex curvature in the first direction. For example, the finger contact surface 112 may be formed to have a curved surface with a semi-cylindrical shape or a semi-elliptical shape.

As the finger contact surface 112 is formed with a curved surface, the finger 10 may be deformed further compared to a flat surface, when an equal force is applied by the finger 10. Accordingly, a less force is required to press the finger contact surface 112 having a curved surface compared to a flat surface, when the finger 10 is deformed equally. However, in another example embodiment, the finger contact surface 112 may be formed with a flat surface.

The texture unit 116 may be disposed at the apex of the finger contact surface 112. The texture unit 116 may be disposed to allow the user to feel a tactile sensation on both portions of the finger 10. The texture unit 116 may have a convex shape.

That is, the texture unit 116 may be formed with a bump having a solid hemisphere shape or a dome shape. Accordingly, as a protruding portion of the bump is formed with a curved surface, a user feels no pain when pressing the bump with the finger 10.

As the size of the bump increases, a stronger tactile sensation may be provided, but pressure applied to the finger 10 may increase. As the size of the bump is reduced, a weaker tactile sensation is provided, but pressure applied to the finger 10 may be reduced.

For example, in order to achieve a good compromise between tactile recognition and pressure, the bump may have a maximum height and diameter in a range of 0.5 mm to 1 mm. However, the bump may have various shapes as long as the bump may provide a tactile sensation. Further, a plurality of bumps may be formed on each of both portions of the finger 10.

The finger contact surface 112 includes: a first light-transmitting area 112a formed on one portion of the finger contact surface 112; a pair of second light-transmitting areas 112b which are spaced apart from both sides of the first light-transmitting area 112a and are formed on another portion of the finger contact surface 112; and a non-light-transmitting area 112c formed on a portion other than the first light-transmitting area 112a and the second light-transmitting areas 112b.

A pulse wave sensor may be disposed inside the interface main body 111, and when the finger 10 is in contact with the finger contact surface 112, the first light-transmitting area 112a may receive light reflected from tissue of the finger 10 and transmit the reflected light toward the pulse wave sensor, so that a photodetector of the pulse wave sensor may detect the reflected light. The second light-transmitting areas 112b transmit light emitted by light sources, so that the transmitted light may be delivered to the tissue of the finger 10 which is in contact with the finger contact surface 112.

The first light-transmitting area 112a has a square outer shape, and may be disposed in the middle of the finger contact surface 112. The second light-transmitting areas 112b each may have a square outer shape, and may be formed as a pair. With respect to a predetermined direction, in which the finger 10 is placed on the finger contact surface 112, the second light-transmitting areas 112b may be spaced apart from both sides of the first light-transmitting area 112a in a direction parallel to a width direction of the finger 10, i.e., in the second direction. The second light-transmitting areas 112b may be spaced apart from the first light-transmitting area 112a at regular intervals.

Each of the second light-transmitting areas 112b may have a smaller area than the first light-transmitting area 112a. The second light-transmitting area 112b may have the same length as the first light-transmitting area 112a in the first direction, and may have a shorter length than the first light-transmitting area 112a in the second direction.

The texture unit 116 may be disposed at the non-light-transmitting area 112c near the first light-transmitting area 112a. Accordingly, when light is transmitted through the first light-transmitting area 112a and the second light-transmitting areas 112b, the texture unit 116 does not block the first light-transmitting area 112a and the second light-transmitting areas 112b, and thus does not affect the measurement of pulse wave signals by the pulse wave sensor.

The texture unit 116 may be disposed at the non-light-transmitting area 112c on each of both sides of the first light-transmitting area 112a, so that when the finger 10 is placed on the finger contact surface 112 in a predetermined direction, the texture unit 116 may allow the user to feel a tactile sensation on each of both portions of the finger 10. Here, the texture unit 116 is disposed at the non-light-transmitting area 112c between the first light-transmitting area 112a and the second light-transmitting area 112b.

The interface main body 111 includes a main body housing 113 and a main body cover 114. The main body housing 113 has an internal space and one open side. The main body cover 114 has the finger contact surface 112 on one side, and covers the open side of the main body housing 113 on the other side.

The main body cover 114 may include a cover member 114a and a light-transmitting members 114b. The cover member 114a has holes corresponding to the first light-transmitting area 112a and the second light-transmitting areas 112b, respectively. The cover member 114a may be made of an opaque material so that light may be transmitted only through the holes.

The cover member 114a may have an intensity level, at which the cover member 114a is not deformed when being pressed by the finger 10. The cover member 114a may be made of a material, such as carbon fiber, high-strength plastic, and the like, which has an intensity of 0.5 GPa or higher.

The cover member 114a may have a convex curvature in the first direction. The cover member 114a may have a predetermined thickness. The texture unit 116 may be formed at a non-light-transmitting portion of the cover member 114a near the holes which form the first light-transmitting area 112a.

The light-transmitting members 114b are inserted into the respective holes of the cover member 114a, thus allowing the main body cover 114 to form the first light-transmitting area 112a, the second light-transmitting areas 112b, and the non-light-transmitting area 112c. The light-transmitting members 114b may be inserted into the holes of the cover member 114a and fixed thereto, thereby forming a smooth finger contact surface 112 along with the cover member 114a.

In the case where the cover member 114a has a convex curvature in the first direction, the light-transmitting members 114b may have the same curvature as the curvature of the cover member 114a. The light-transmitting member 114b may be made of glass, transparent plastic, and the like. The light-transmitting member 114b may have a predetermined thickness.

The main body housing 113 may be made of an opaque material. Accordingly, in the case where the pulse wave sensor is embedded in the main body housing 113, the main body housing 113 may allow light transmission only through the first light-transmitting area 112a and the second light-transmitting areas 112b. The main body housing 113 may be made of the same material as the cover member 114a. The main body housing 113 may be manufactured and assembled separately from the cover member 114a, but may also be integrally formed with the cover member 114a.

The main body housing 113 may accommodate light sources and photodetectors of the pulse wave sensor in internal spaces which are divided by partition walls 113a. The partition walls 113a may block light, emitted by the light sources, from entering the photodetectors.

The partition wall 113a may be made of an opaque material as in the main body housing 113. The partition wall 113a is arranged across the holes of the cover member 114a. Further, the partition wall 113a may be connected to an inner portion of the cover member 114a, so as to prevent leakage of light through a space between the partition wall 113a and the cover member 114a. The partition wall 113a may be integrally formed with the main body housing 113. The texture unit 116 may be disposed on the top surface of the partition wall 113a to be protruded from the level at which the first light-transmitting area 112a and the second light-transmitting areas 112b are positioned. Alternatively, the texture unit 116 may be formed by having the top surface of the partial wall 113a positioned lower than the level at which the first light-transmitting area 112a and the second light-transmitting areas 112b are positioned, or may be formed by creating a cut, depression, or recess on the top surface of the partial wall 113a.

Figure 6:
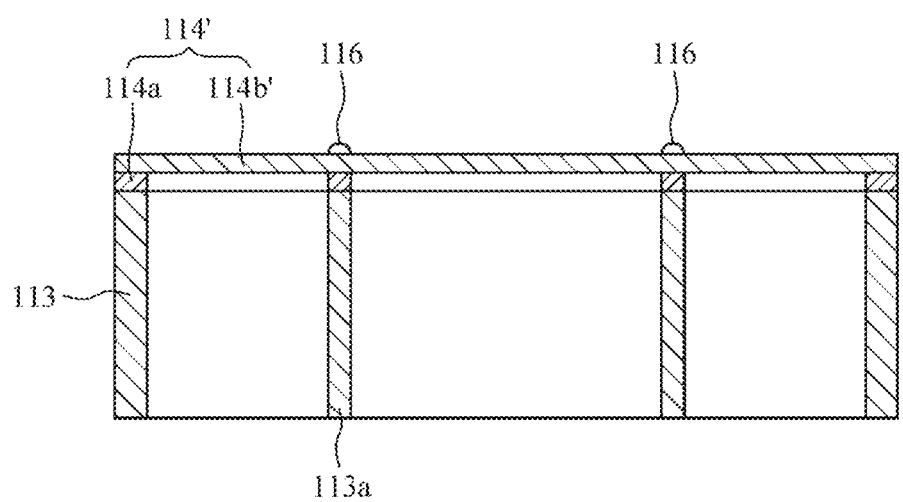
FIG. 6 is a cross-sectional view of a texture interface including a main body cover according to another example embodiment.

In another example, as illustrated in FIG. 6, a main body cover 114' includes: a cover member 114a having holes, the size of which corresponds to each of the first light-transmitting area 112a and the second light-transmitting areas 112b; and a light-transmitting member 114b' which entirely covers the cover member 114a. The cover member 114a may be formed in the same manner as described above. The light-transmitting member 114b' may have the same area as the cover member 114a, and may entirely cover the cover member 114a, thereby allowing the main body cover 114' to form the first light-transmitting area 112a, the second light-transmitting areas 112b, and the non-light-transmitting area 112c.

The light-transmitting member 114b' has an outer surface which forms the finger contact surface 112. In this case, the texture unit 116 may be formed at the outer surface of the light-transmitting member 114' to correspond to a portion around the holes forming the first light-transmitting area 112a. As the outer surface of the light-transmitting area 114b' has a smooth surface, the finger contact surface 112 may be formed with a smooth surface.

In the case where the cover member 114a has a convex curvature in the first direction, the light-transmitting member 114b' also have the same curvature as the curvature of the cover member 114a. The light-transmitting member 114b' may be made of glass, transparent plastic, and the like, and may have a predetermined thickness.

Figure 7:
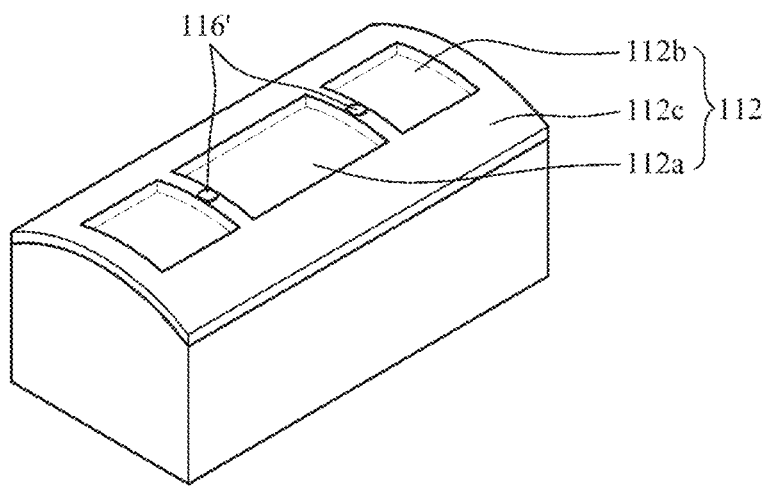
FIG. 7 is a perspective view of a texture interface including a texture unit according to yet another example embodiment.
Figure 8:
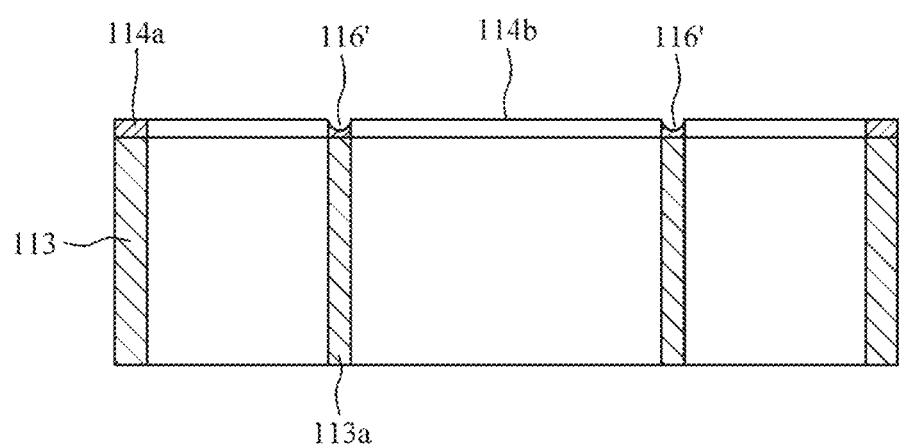
FIG. 8 is a cross-sectional view of the texture unit illustrated in FIG. 7.

In yet another example, as illustrated in FIGS. 7 and 8, a texture unit 116' may have a concave shape. For example, the texture unit 116' may be formed with a groove having a hemisphere shape or a dome shape. As the size of the groove increases, a stronger tactile sensation may be provided, but pressure applied to the finger 10 may increase. As the size of the groove is reduced, a weaker tactile sensation is provided, but pressure applied to the finger 10 may be reduced.

For example, in order to achieve a good compromise between tactile recognition and pressure, the groove may have a maximum depth and diameter in a range of 0.5 mm to 1 mm. However, the groove may have various shapes as long as the groove may provide a tactile sensation. Further, a plurality of grooves may be formed on each of both portions of the finger 10.

Figure 9:
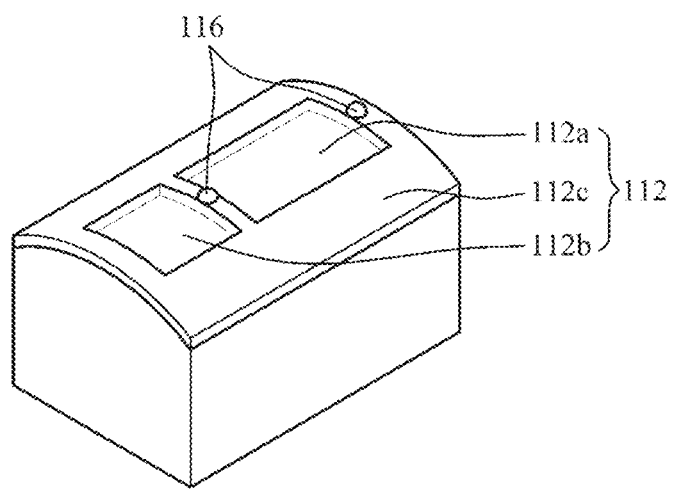
FIG. 9 is a perspective view of a texture interface including an interface main body according to yet another example embodiment.

In still another example, as illustrated in FIG. 9, any one of the two second light-transmitting areas 112b may be omitted from the finger contact surface 112. In this case, each position of the first light-transmitting area 112a and the second light-transmitting area 112b may be changed according to the area of the finger contact surface 112. The texture unit 116 may be disposed at the non-light-transmitting area 112c near the first light-transmitting area 112a. The texture unit 116 may be disposed at the non-light-transmitting area 112c on each of both sides of the first light-transmitting area 112a, so that when the finger 10 is placed on the finger contact surface 112 in a predetermined direction for contact with the finger contact surface 112, the texture unit 116 may allow the user to feel a tactile sensation on both portions of the finger 10. Instead of the texture unit 116 having a bump shape, the texture unit 116' having a groove shape may be provided.

In another example embodiment, the texture unit 116 may have the same curvature as the finger contact surface 112 when the finger contact surface 112 is curved, but may have a different texture than the finger contact surface 112. For example, the texture unit 116 may have a gritty and/or rough texture like sandpaper while the finger contact surface 112 has a smooth texture. When the finger contact surface 112 is a flat and even surface, the texture unit 115 may have the same level as the finger contact surface 112 while having a different texture than the finger contact surface 112.

Figure 10:
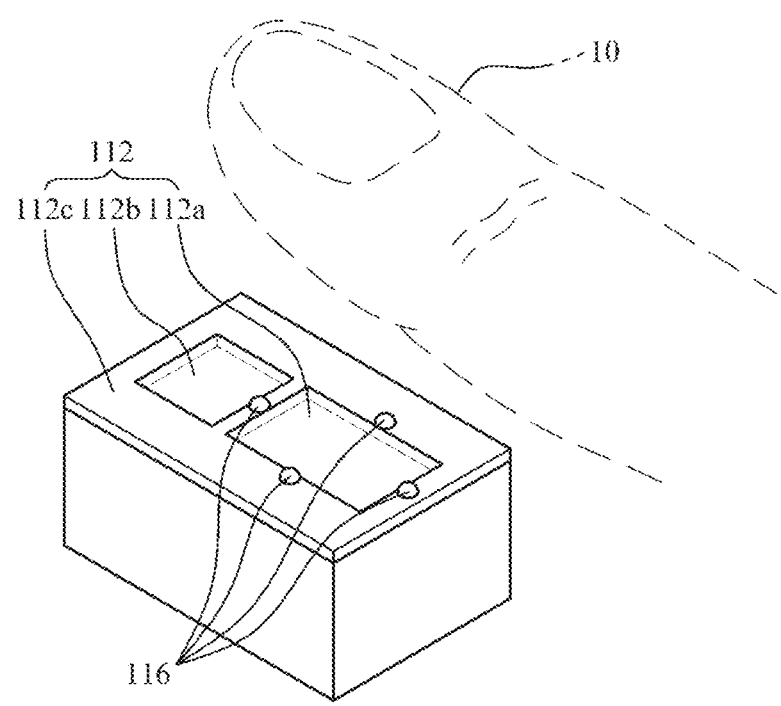
FIG. 10 is a perspective view of a texture interface including an interface main body according to still another example embodiment.

In yet another example, as illustrated in FIG. 10, the finger contact surface 112' includes the first light-transmitting area 112a and the second light-transmitting area 112b which are arranged in a direction parallel with the longitudinal direction of the finger 10, i.e., the first direction, with respect to a predetermined direction in which the finger 10 is placed on the finger contact surface 112'. In this case, the finger contact surface 112' may be formed with a flat surface.

Here, the texture unit 116 may be disposed at the non-light-transmitting area 112c near the first light-transmitting area 112a. The texture unit 116 may be disposed at the non-light-transmitting area 112c on each of both sides of the first light-transmitting area 112a to surround the first light-transmitting area 112. When the finger 10 is placed on the finger contact surface 112' in a predetermined direction for contact with the finger contact surface 112', the texture unit 116 may allow the user to feel a tactile sensation on both portions of the finger 10. The texture unit 116 may be disposed at the non-light-transmitting area 112c on each of a front end and a rear end of the first light-transmitting area 112a, so that the texture unit 116 may allow the user to feel a tactile sensation on both a front end portion and a rear end portion of the finger 10 based on the center of the finger 10.

As described above, at least one texture unit 116 may be disposed on each of four sides of the first light-transmitting area 112a. However, this is merely an example, and the texture units 116 for providing a tactile sensation to each of the front end portion and the rear end portion of the finger 10 may be omitted, or the texture units 116 for providing a tactile sensation to both end portions of the finger 10 may be omitted.

In the embodiment, a pair of the second light-transmitting areas 112b is provided and spaced apart with the first light-transmitting area 112a disposed therebetween, but one of the two second light-transmitting areas 112b may be omitted. Instead of the texture unit 116 having a bump shape, the texture unit 116' having a groove shape may be provided. Further, the finger contact surface 112' may be formed in a smaller size than the size of the distal phalanx of the finger 10, so that the finger 10 may be placed on the finger contact surface 112' having a predetermined contact area, but the size of the finger contact surface 112' is not limited thereto.

Figure 11:
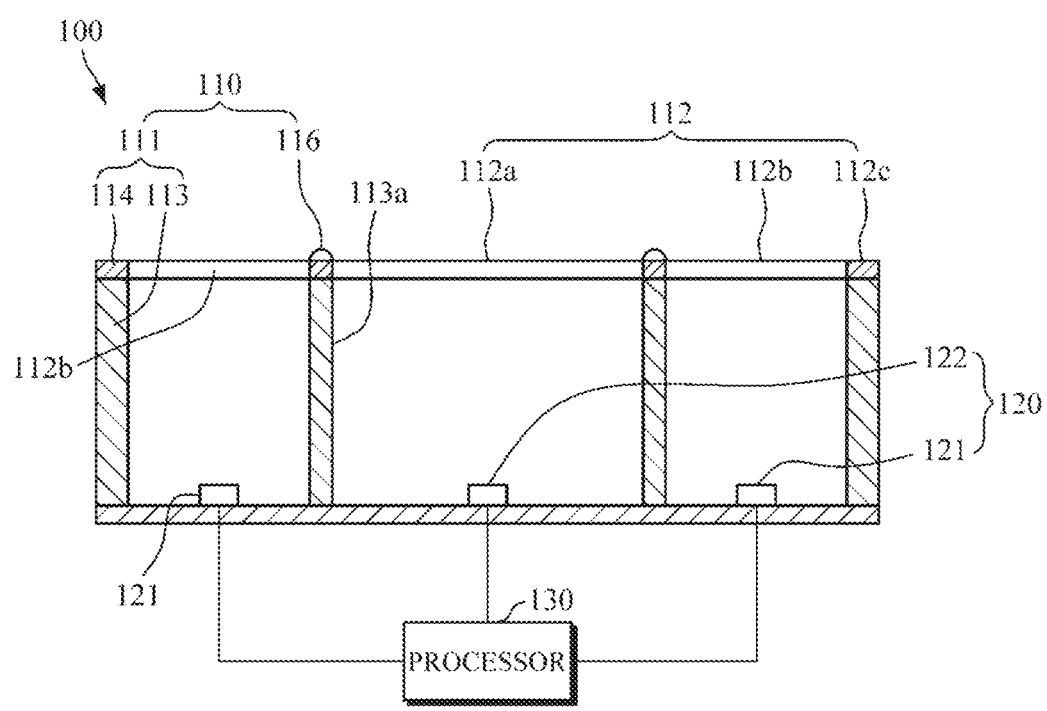
FIG. 11 is a diagram illustrating a bio-signal measuring apparatus according to an example embodiment.

FIG. 11 is a diagram illustrating a bio-signal measuring apparatus according to an example embodiment of the present disclosure.

Referring to FIG. 11, the bio-signal measuring apparatus 100 includes a texture interface 110, a pulse wave sensor 120, and a processor 130. The pulse wave sensor 120 may be also referred to as an optical sensor or a spectrometer.

The texture interface 110 includes an interface main body 111 and a texture unit 116. The interface main body 111 includes a finger contact surface 112, which has a light-transmissive portion, and on which a user's finger 10 is placed for contact with the finger contact surface 112. The texture unit 116 is formed at the finger contact surface 112, so that when the finger 10 is in contact with the finger contact surface 112, the texture unit 116 may allow the user to feel a tactile sensation on the finger 10.

When the finger 10 is in contact with the finger contact surface 112, the finger contact surface 112 may transmit light, emitted by a light source 121 of the pulse wave sensor 120, through a light-transmissive area to the tissue of the finger 10, and may transmit light, reflected from the tissue of the finger 10, through the light-transmissive area to a photodetector 122 of the pulse wave sensor 120.

As described above, the finger contact surface 112 includes the first light-transmitting area 112a, at least one second light-transmitting area 112b, and the non-light-transmitting area 112c. The finger contact surface 112 may have a convex curvature in the first direction. Instead of the finger contact surface 112 having a curved surface, the finger contact surface 112' having a flat surface may be provided.

Here, the texture unit 116 may be disposed at the non-light-transmitting area 112c near the first light-transmitting area 112a. The texture unit 116 may be configured in the same manner as described above. Instead of the texture unit 116 having a bump shape, the texture unit 116' having a groove shape may be provided.

As described above, the interface main body 111 includes the main body housing 113 and the main body cover 114. The main body housing 113 has an internal space and one open side. The main body housing 113 may accommodate the light source 121 and the photodetector 122 of the pulse wave sensor in internal spaces which are divided by the partition walls 113a. The partition walls 113a may block light, emitted by the light source 121, from entering the photodetector 122.

The main body cover 114 has the finger contact surface 112 on one side, and covers the open side of the main body housing 113 on the other side. The main body cover 114 may be configured in the same manner as described above. Instead of the main body cover 114, the main body cover 114' described above may be provided.

The pulse wave sensor 120 measures a pulse wave signal from a user while the finger 10 is in contact with the texture interface 110. Here, the pulse wave signal may be a photoplethysmography (PPG) signal.

The pulse wave sensor 120 includes the light source 121 and the photodetector 122. The light source 121 emits light onto the tissue of the finger 10, which is in contact with the finger contact surface 112, through the second light-transmitting areas 112b. The light source 121 may be two in number, so that the two light sources 121 may be disposed to correspond to the second light-transmitting areas 112b. The light sources 121 may emit light of different wavelengths. The light source 121 may include at least one of a light emitting diode (LED), a laser diode, and phosphor, but is not limited thereto.

The light sources 121 may be driven in a time-division manner under the control of the processor 130, to sequentially emit light onto the finger 10. In this case, light source driving conditions, such as an emission time, a driving sequence, a current intensity, a pulse duration, and the like of the light sources 121 may be preset. The processor 130 may control driving of the light sources 121 by referring to the light source driving conditions.

The photodetector 122 detects light, reflected from the tissue of the finger 10 which is in contact with the finger contact surface 112, through the first light-transmitting area 112a. The photodetector 122 may include a photodiode. The photodetector 112 may measure a first pulse wave signal and a second pulse wave signal by sequentially detecting light of different wavelengths sequentially emitted by the light sources 121 onto the finger 10 and emanating from the tissue of the finger 10.

According to one or more example embodiments, a biosignal measuring apparatus 100 may include: an optical sensor including at least one light source 121 and at least one photodetector 122; and a housing that covers only the optical sensor or both the optical sensor and the bio-signal measuring apparatus 100, and includes a finger contact surface 112. In a case in which the finger contact surface 112 is divided into at least two areas 112a and 112b which are spaced apart from each other, and the at least one light source 121 and the at least one photodetector 122 may be disposed directly underneath the at least two areas 112a and 112b of the finger contact surface 112, respectively, and at least one texture unit 116 may be arranged at a boundary between the two areas 112a and 112b of the finger contact surface 112. In a case in which the finger contact surface 112 is formed as a single integrated area without a partition separating the finger contact surface 112 into one or more areas, the at least one texture 116 (e four texture units 116) may be a ranged along a boundary of the finger contact surface 112. The at least one texture unit 116 may be protruded from the finger contact surface 112, or depressed below the finger contact surface 112 so that a user can recognize the location of the texture unit 116 and adjust the position of his/her finger with reference to guide information provided from the bio-signal measuring apparatus 100. In another example, the at least one texture unit 116 has the same curvature or the same flat level as the finger contact surface 112, but has a different texture than the finger contact surface 112.

Figure 12:
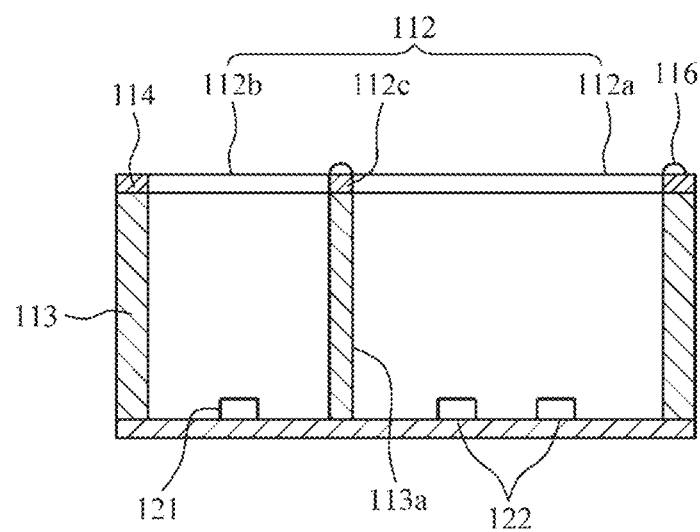
FIG. 12 is a diagram illustrating another example of a pulse wave sensor.

In another example, as illustrated in FIG. 12, the pulse wave sensor 120 may include one light source 121 and two photodetectors 122. In this case, one of the two second light-transmitting areas 112b may be omitted from the finger contact surface 112. The light source 121 may emit light of a single wavelength onto the finger 10. The light source 121 may emit light in a broad wavelength range including a visible light range.

In response to the light of a single wavelength emanating from the finger 10, the photodetectors 122 may measure a plurality of pulse wave signals. To this end, the photodetectors 122 may be formed to have a plurality of different response characteristics.

For example, the photodetectors 122 may be photodiodes having different measurement ranges so as to respond to light of different wavelengths. Alternatively, different color filters may be provided for the photodetectors 122 to respond to light of different wavelengths, or a color filter may be provided for only one of the photodetectors 122.

The photodetectors 122 may be positioned at different distances from the light source 121, in which the photodetector 122 disposed at a relatively short distance from the light source 121 detects light in a short wavelength range, and the photodetector 172 disposed at a relatively long distance from the light source 121 may detect light in a long wavelength range.

Alternatively, the photodetectors 122, which are positioned at different distances from the light source 121, may detect light of the same wavelength. In this case, penetration depth of light into the tissue of the finger 10, after the light is detected by each of the photodetectors 122, may be determined according to a distance between the photodetectors 122 and the light source 121.

Embodiments of the pulse wave sensors 120 for measuring pulse wave signals of different wavelengths are merely exemplary, and the pulse wave sensor 120 is not limited by the number of the light source 121 and the photodetector 122 and the like. Further, various embodiments of acquiring pulse wave signals by differentiating signals according to a pulse wave source depth may also be provided.

The processor 130 may estimate bio-information based on a pulse wave signal measured by the pulse wave sensor 120. The processor 130 may obtain an oscillometric waveform by using a plurality of pulse wave signals measured by the pulse wave sensor 120. In this case, the plurality of pulse wave signals may be pulse wave signals having different wavelengths, but are not limited thereto, and the processor 130 may obtain the oscillometric waveform by using a plurality of pulse wave signals having the same wavelength.

The processor 130 may estimate bio-information based on the obtained oscillometric waveform, in this case, the bio-information may include blood pressure, vascular age, arterial stiffness, aortic pressure waveform, stress index, degree of fatigue, and the like, but is not limited thereto. However, for convenience of explanation, the following description will be made using blood pressure as an example.

For example, once the plurality of pulse wave signals are measured, the processor 130 may subtract a second signal related to a pulse wave signal having a short wavelength from a first signal related to a pulse wave signal having a relatively long wavelength, and may obtain the oscillometric waveform based on a differential signal. In this case, the first signal may be the measured pulse wave signal having a long wavelength, or may be a differentiated signal obtained by differentiating the pulse wave signal having a long wavelength according to a predetermined order of differentiation. Likewise, the second signal may be the measured pulse wave signal having a short wavelength, or may be a differentiated signal obtained by differentiating the pulse wave signal having a short wavelength according to a predetermined order of differentiation.

Further, upon obtaining the oscillometric waveform, the processor 130 may extract a characteristic point from the oscillometric waveform, and may measure blood pressure by applying the extracted characteristic point to a blood pressure measurement model. For example, the processor 130 may extract an amplitude value at a maximum peak point of the oscillometric waveform as a characteristic point for calculating mean arterial pressure. Further, the processor 130 may extract amplitude values at the right and left points, which are symmetrically distant from the amplitude value at the maximum peak point and which have a preset peak ratio within a range from 0.5 to 0.7, as characteristic points for calculating systolic blood pressure (SBP) and diastolic blood pressure (DBP).

Figure 13:
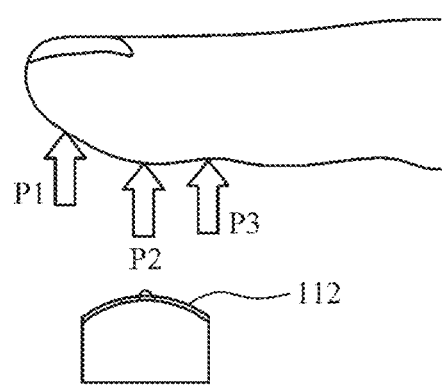
FIG. 13 is a diagram illustrating each position of the underside of a finger placed in a set position on a finger contact surface.
Figure 14:
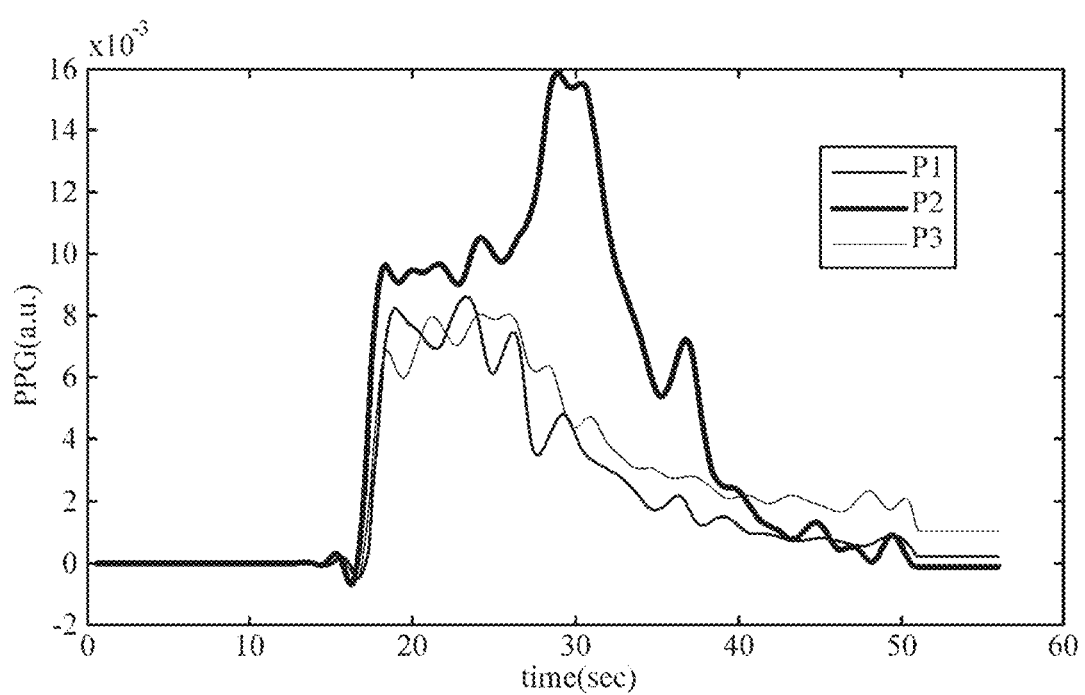
FIG. 14 is a graph showing oscillometric waveforms obtained at each position of the underside of the finger of FIG.

As described above, the processor 130 may measure blood pressure by using the oscillometric waveform. As illustrated in FIGS. 13 and 14, contact force between the finger contact surface 112 and the finger 10 may vary depending on which portion of the finger 10, among a front portion P1, a middle portion P2, and a rear portion P3 on the underside of the finger 10, comes into contact with a set position on the finger contact surface 112, and a peak position of the oscillometric waveform is changed due to a difference of the contact force between the finger contact surface 112 and the finger 10.

Accordingly, every time a user measures bio-signals at different times, the user is required to place a specific portion of the underside of the finger 10 in a set position on the finger contact surface 112 for contact with the finger contact surface 112, so as to obtain a stable and consistent oscillometric waveform under the same health condition of the user.

In this case, the texture interface 110 may induce a user to place a specific ion of the underside of the finger 10 in the set position on the finger contact surface 112 every time the user measures a bio-signal at different times. Accordingly, reproducibility of the oscillometric waveform may be improved, and health indicators of the user may be estimated accurately under the same health condition of the user.

In addition, as compared with a solid interface having no texture units 116 and 116', the texture interface 110 of the present disclosure has an effect in that a constant PPG waveform may be obtained every time a user measures bio-signals at different times, thereby improving reproducibility of the PPG waveform.

In this respect, the following description will be made with reference to FIGS. 15A to 16B based on a result of comparison test between the texture interface and the solid interface. In the test process, a robot apparatus was used to induce a finger to apply a constant contact force to a finger contact surface.

Figure 15A:
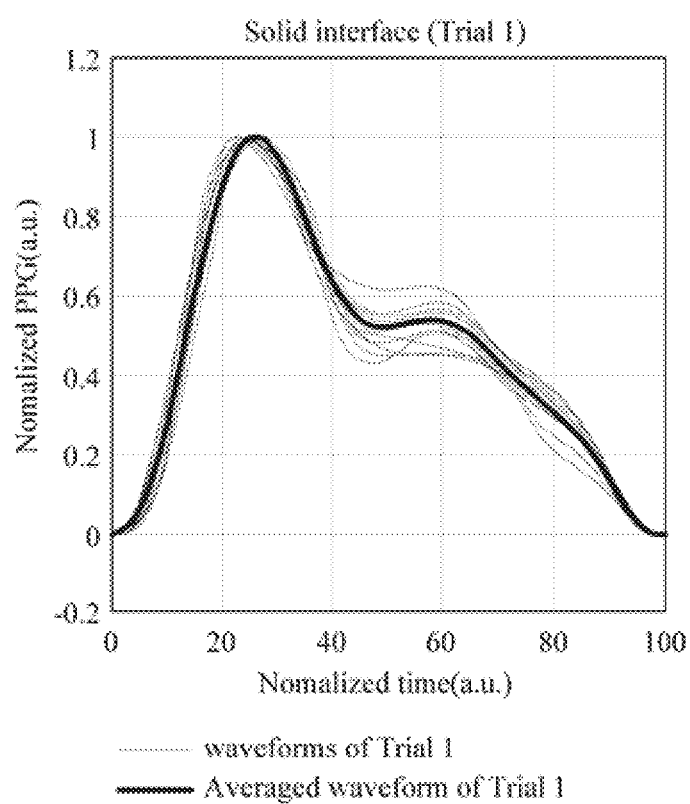
FIG. 15A is a graph showing PPG waveforms obtained in trial 1 for a solid interface in a comparative example.
Figure 15B:
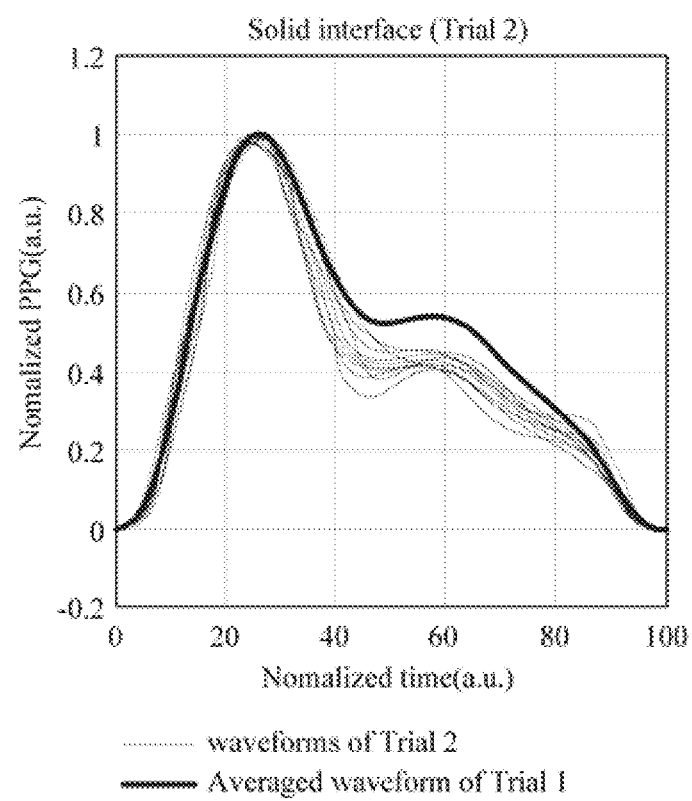
FIG. 15B is a graph showing PPG waveforms obtained in trial 2 for a solid interface in a comparative example.
Figure 16A:
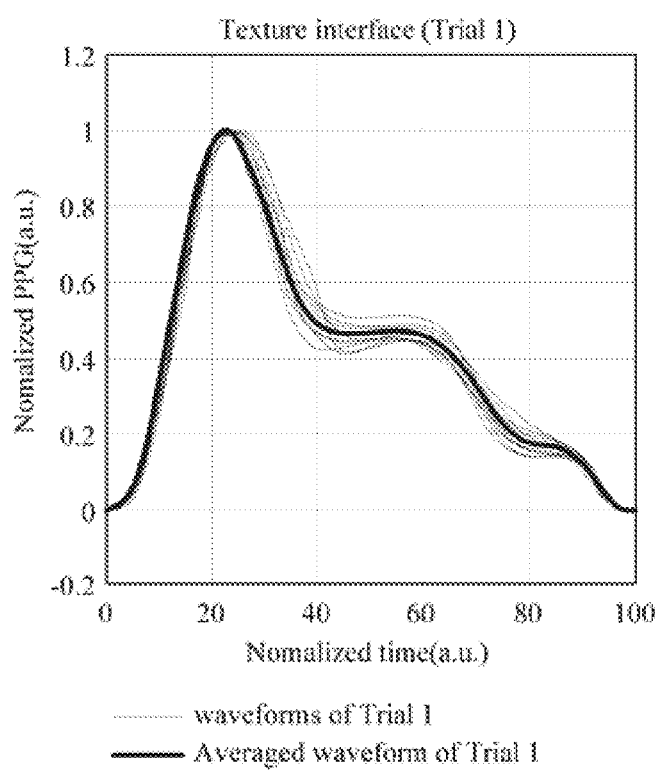
FIG. 16A is a graph showing PPG waveforms obtained in trial 1 for a texture interface according to an example embodiment.

FIG. 15A is a graph showing PPG waveforms obtained in trial 1 for a solid interface in a comparative example; and FIG. 15B is a graph showing PPG waveforms obtained in trial 2 for a solid interface in a comparative example. FIG. 16A is a graph showing PPG waveforms obtained in trial 1 for a texture interface according to an example embodiment of the present disclosure; and FIG. 16B is graph showing PPG waveforms obtained in trial 2 for a texture interface according to an example embodiment of the present disclosure.

More specifically, thin lines in FIG. 15A indicate a plurality of PPG waveforms measured in trial 1 for the solid interface in a comparative example, and a thick line indicates an averaged waveform obtained by averaging the PPG waveforms; and thin lines in FIG. 15B indicate a plurality of PPG waveforms measured in trial 2 for the solid interface in a comparative example, and a thick line indicates an averaged waveform of trial 1 shown in FIG. 15A.

Figure 16B:
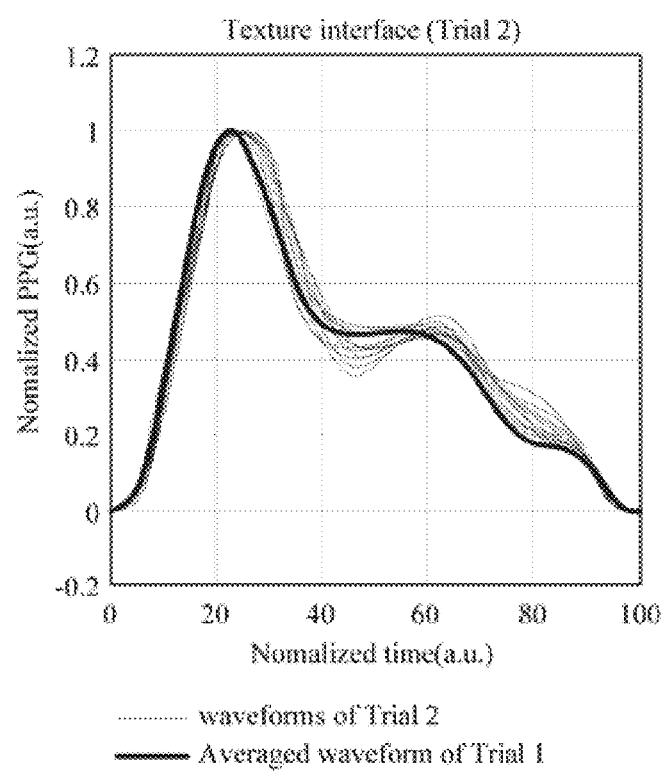
FIG. 16B is graph showing PPG waveforms obtained in trial 2 for a texture interface according to an example embodiment.

Thin lines in FIG. 16A indicate a plurality of PPG waveforms measured in trial 1 for the texture interface according to an example embodiment of the present disclosure, and a thick line indicates an averaged waveform obtained by averaging the PPG waveforms; and thin lines in FIG. 16B indicate a plurality of PPG waveforms measured in trial 2 for the texture interface according to an example embodiment of the present disclosure, and a thick line indicates an averaged waveform of trial 1 shown in FIG. 16A.

In the solid interface of FIG. 15B, all the PPG waveforms of trial 2 have different amplitudes from the averaged waveform of trial 1 at the center of the waveforms. By contrast, in the texture interface of FIG. 16B, all the PPG waveforms of trial 2 have similar amplitudes to the averaged waveform of trial 1 at the center of the waveforms.

By evaluating similarity using a root mean squared error between the PPG waveforms and the averaged waveform along with an average correlation coefficient between the PPG waveforms and the averaged waveform, it can be seen that the average correlation coefficient of the texture interface is greater than the average correlation coefficient of the solid interface, and the root mean squared error of the texture interface is smaller than the root mean squared error of the solid interface. Accordingly, it can be concluded that PPG waveforms obtained in different trials may be more constant in the texture interface than the solid interface.

Figure 17:
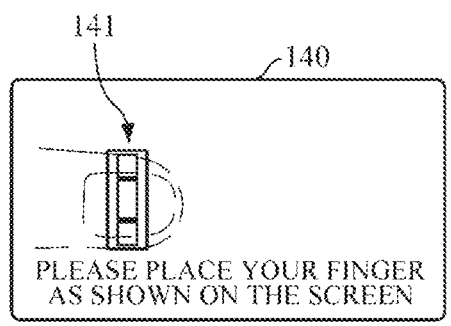
FIG. 17 is a diagram illustrating an example of outputting action guide information to an outputter.

As illustrated in FIG. 17, the bio-signal measuring apparatus 100 may further include an outputter 140. Upon receiving a request for measuring a bio-signal, the processor 130 may output, through the outputter 140, action guide information 141 for guiding a finger 10 to come into contact with the finger contact surface 112. The action guide information 141 may include a text and/or a visual image for guiding a position of the finger 10 to the finger contact surface 112. Further, the action guide information 141 may include a text and/or a visual image, a voice message, and the like to indicate the start of bio-signal measurement.

The outputter 140 may visually output the action guide information 141 on a display panel, or may non-visually output the information 141 by voice, vibrations, tactile sensation, and the like using a speaker module, a haptic module, and the like. In this case, if an estimated bio-information value falls outside a normal range, the outputter 140 may output warning information in various manners, such as highlighting an abnormal value in red and the like, displaying the abnormal value along with a normal range, outputting a voice warning message, adjusting a vibration intensity, and the like.

Figure 18:
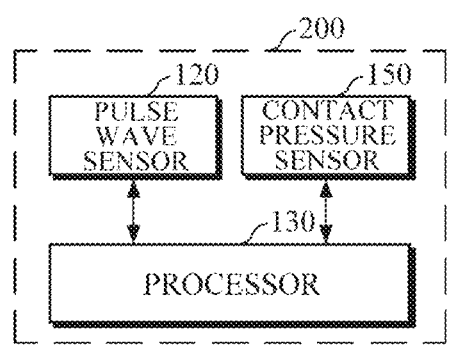
FIG. 18 is a block diagram illustrating a bio-signal measuring apparatus according to an example embodiment.

FIG. 18 is a block diagram illustrating a bio-signal measuring apparatus according to an example embodiment of the present disclosure.

Referring to FIG. 18, the bio-signal measuring apparatus 200 may further include a contact pressure sensor 150. The contact pressure sensor 150 may be layered with the pulse wave sensor 120, so as to measure contact pressure applied by the finger 10 to the finger contact surface 112. The contact pressure sensor 150 may be composed of a force sensor and a contact area measuring sensor, or may be composed of a force sensor and a capacitive sensor array, but is not specifically limited thereto.

Figure 19:
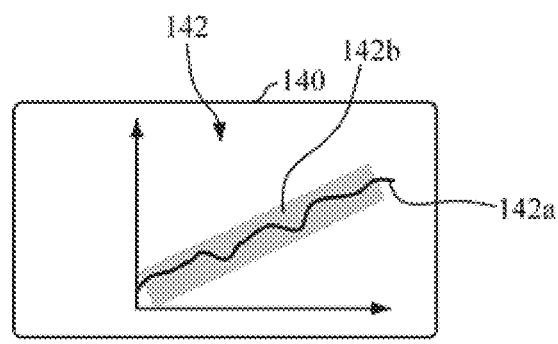
FIG. 19 is a diagram illustrating an example of outputting pressure guide information to an outputter as illustrated in FIG. 18.

In this case, as illustrated in FIG. 19, the action guide information 141 may include pressure guide information 142 for inducing a change in contact pressure to increase or decrease the contact pressure applied by the finger 10 to the finger contact surface. The outputter 140 may visually output the pressure guide information 142 on a display panel.

For example, the pressure guide information 142 may include information for inducing a gradual increase in contact pressure 142*a* while the finger 10 is in contact with the finger contact surface 112; or information on reference contact pressure 142*b* for inducing a gradual decrease in the contact pressure 142*a* when the initial contact pressure 142*a* equal to or greater than a predetermined threshold value is applied. In this case, information on the reference contact pressure 142*b* may include a reference contact pressure value at each measurement time or a range of reference contact pressure values.

Figure 20:
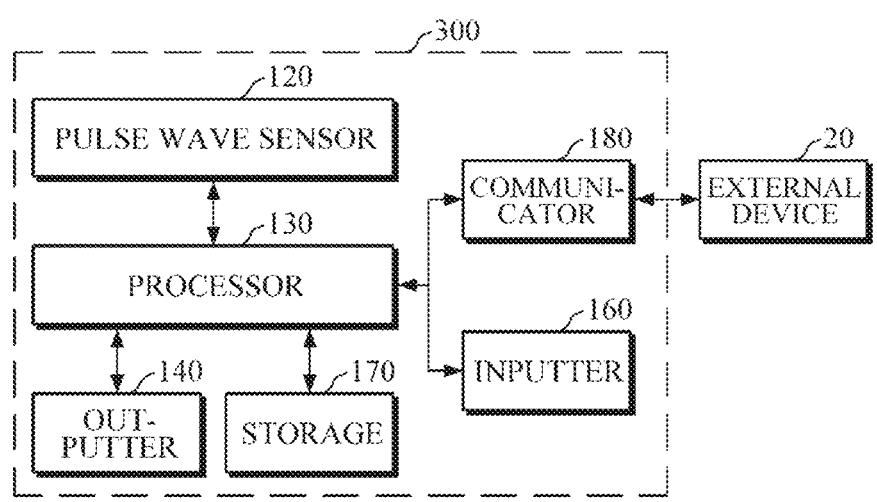
FIG. 20 is a block diagram illustrating a bio-signal measuring apparatus according to an example embodiment. We do not recommend using the words "a first embodiment" "a second embodiment," etc. because when we want to combine some of the features in the first, second, and third embodiments, the Examiner may raise a support issue.

FIG. 20 is a block diagram illustrating a bio-signal measuring apparatus according to an example embodiment.

Referring to FIG. 20, the bio-signal measuring apparatus 300 according to the example embodiment may further include an inputter 160, a storage 170, and a communicator 180. The inputter 160 may receive input of various operation signals, such as a request for measuring a bio-signal, from a user. For example, the inputter 160 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 170 may store programs or commands for operation of the bio-signal measuring apparatus 300, and may store data input to and output from the bio-signal measuring apparatus 300. Further, the storage 170 may store data processed by the bio-signal measuring apparatus 300, data required for data processing of the bio-signal measuring apparatus 300, e.g., a bio-information estimation model, and the like.

The storage 170 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the bio-signal measuring apparatus 300 may operate an external storage medium, such as web storage and the like, which performs a storage function of the storage 170 on the Internet.

The communicator 180 may perform communication with an external device 20. For example, the communicator 180 may transmit, to the external device 20, data managed by the bio-signal measuring apparatus 300, processing result data of the bio-signal measuring apparatus 300, and the like, or may receive, from the external device 20, various data useful or helpful for measuring bio-signals and/or for estimating bio-information.

Here, the external device 20 may be medical equipment using the data managed by the bio-signal measuring apparatus 300, the processing result data of the bio-signal measuring apparatus 300, and the like, a printer to print out results, or a display to display the results. In addition, the external device 20 may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 180 may communicate with the external device 20 by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bio-signal measuring apparatus, comprising:
   a main body housing comprising a plurality of walls that divide an internal space of the main body housing into a plurality of regions;
   a main body cover that covers the internal space of the main body housing and comprising a finger contact surface configured to be in contact with a finger of a user;
   an optical sensor comprising at least one light source and at least one light detector that are disposed underneath the finger contact surface, in the plurality of regions divided by the plurality of walls, respectively; and
   a plurality of textured areas formed on the finger contact surface directly above the plurality of walls of the main body housing, wherein each of the plurality of textured areas comprises a plurality of protrusions or a plurality of recesses, or has a different roughness from a remaining area of the finger contact surface,
   wherein the finger contact surface is curved to have a constant curvature, and the textured area is disposed at an apex portion of the finger contact surface.

2. The bio-signal measuring apparatus of claim 1, wherein the finger contact surface comprises:
   a first light-transmitting area formed on a first portion of the finger contact surface;
   at least one second light-transmitting area which is spaced apart from the first light-transmitting area and is formed on a second portion of the finger contact surface; and
   a non-light-transmitting area formed on a third portion of the finger contact surface other than the first light-transmitting area and the second light-transmitting area.

3. The bio-signal measuring apparatus of claim 2, wherein the textured area is disposed in the non-light-transmitting area.

4. The bio-signal measuring apparatus of claim 3, wherein the textured area comprises the plurality of protrusions disposed to surround the first light-transmitting area.

5. The bio-signal measuring apparatus of claim 3, wherein the textured area comprises the plurality of recesses disposed to surround the first light-transmitting area.

6. The bio-signal measuring apparatus of claim 1, wherein the main body cover comprises:
   a cover member having holes, a size of which corresponds to each of the plurality of regions divided by the plurality of walls; and
   a light-transmitting member disposed inside each of the holes of the cover member.

7. The bio-signal measuring apparatus of claim 1, wherein the main body cover comprises:
- a cover member having holes, a size of which corresponds to each of the plurality of regions divided by the plurality of walls; and
- a light-transmitting member which entirely covers the cover member.

8. The bio-signal measuring apparatus of claim 1, wherein the optical sensor is a pulse wave sensor configured to measure a pulse wave signal from the user when the finger is in contact with the finger contact surface, and
- wherein the bio-signal measuring apparatus further comprises a processor configured to obtain bio-information based on the pulse wave signal measured by the pulse wave sensor.

9. The bio-signal measuring apparatus of claim 8, wherein the finger contact surface comprises:
- a first light-transmitting area formed on a first portion of the finger contact surface;
- at least one second light-transmitting area which is spaced apart from the first light-transmitting area and is formed on a second portion of the finger contact surface; and
- a non-light-transmitting area formed on a third portion of the finger contact surface other than the first light-transmitting area and the second light-transmitting area.

10. The bio-signal measuring apparatus of claim 9, wherein:
- the at least one light source is configured to emit light onto tissue of the finger when the finger is in contact with the finger contact surface through the second light-transmitting area; and
- the at least one detector is configured to detect the light reflected from the tissue of the finger when the finger is in contact with the finger contact surface through the first light-transmitting area.

11. The bio-signal measuring apparatus of claim 8, wherein the pulse wave signal is a photoplethysmography (PPG) signal.

12. The bio-signal measuring apparatus of claim 8, wherein upon receiving a request for measuring a bio-signal, the processor outputs action guide information for guiding the user to place the finger into contact with the finger contact surface.

* * * * *